United States Patent [19]

Ghodse

[11] Patent Number: 6,110,926
[45] Date of Patent: Aug. 29, 2000

[54] EYEDROP COMPOSITION

[75] Inventor: Abdol Hamid Ghodse, London, United Kingdom

[73] Assignee: St. George's Enterprises Limited, London, United Kingdom

[21] Appl. No.: 09/133,816

[22] Filed: Aug. 13, 1998

[51] Int. Cl.$^7$ ...................................................... A67K 31/44
[52] U.S. Cl. ........................................... 514/289; 514/912
[58] Field of Search ...................... 514/289, 912

[56] References Cited

PUBLICATIONS

Sanchez–Ramos et al., British Journal of Addiction, 82(3):313–315 (1987).
Ghodse et al., British Journal of Psychiatry, 148:44–46 (1986).
Jones, Eastern Pharmacist, 26(302):55–58 (1983).

*Primary Examiner*—Zohreh Fay
*Attorney, Agent, or Firm*—Bacon & Thomas

[57] ABSTRACT

An eyedrop composition comprising a solution of naloxone hydrochloride in a mixture of water and at least one pharmaceutically acceptable polyhydric alcohol which is stable over long periods of time and is useful in opioid addiction testing

6 Claims, No Drawings

EYEDROP COMPOSITION

This invention relates to naloxone hydrochloride and in particular to aqueous naloxone hydrochloride formulations useful as eyedrops.

Naloxone hydrochloride is a specific and effective opioid antagonist which acts competitively at opioid receptors and has been found to have a wide variety of medical uses, for example in reversal of the effects of therapeutic or overdose quantities of opioid drugs. Thus, intravenous naloxone hydrochloride may be used in diagnosis and treatment of opioid overdosage and may be administered post-operatively to reverse central nervous system depression resulting from the use of opioids during surgery.

One particularly useful application of naloxone hydrochloride is in the opioid addiction test developed by Ghodse and co-workers, as reported in *Br. J. Psychiatry* 148, pp. 44–46 (1986) and *The Lancet* 333, pp. 748–750 (1989). This is based on measurement of pupillary response to topically instilled naloxone hydrochloride eyedrops, it having been found that instillation of such an eyedrop into the conjunctival sac of one eye of an opioid dependent subject causes pupil dilatation (mydriasis) in that eye only. This response is not observed either in non-opioid dependent subjects given opioid injections prior to minor surgery or in subjects with no history of opioid use.

Accordingly, the test involves measurement of anisocoria (the size difference between the left and right pupils) before and after (optimally about 40 minutes after) administration of naloxone hydrochloride solution to one eye only, a relative increase in pupil size for the treated eye being evidence of opioid dependency. The results may be determined from photographs of the eyes but are preferably obtained using a binocular electronic pupillometer as described in WO-A-94/07406.

Initial work on this test was performed using 0.1% w/v solutions of naloxone hydrochloride formulated for injection. However, such solutions have a pH of about 3 and, by virtue of their acidity, cause painful stinging when applied to the eye; this is normally accompanied by reflex tear formation and rapid blinking, causing rapid clearance of the solution from the eye. Solutions in 0.9% w/v saline or isotonic pH 6.5 phosphate buffer have therefore been employed to avoid this reaction. Use of such solutions has, however, been found to lead to inconsistencies in the test results, a fact which may explain the report by Loimar et al (*The Lancet* May 5, 1990, pp. 1107–1108) that conjunctival naloxone does not provide a decision aid in determining opioid addiction. Tests have shown that such solutions are in fact unstable, the naloxone content degrading by hydrolysis over the course of a few days. In order to facilitate use of the opioid addiction test, there is therefore a need for naloxone hydrochloride formulations which may be administered to the eye without discomfort and which exhibit long term storage stability, e.g. for one year or more.

The present invention is based on the finding that polyhydric alcohols may be incorporated into aqueous solutions of naloxone hydrochloride to give ophthalmically acceptable formulations with enhanced storage stability relative to previously proposed ophthalmic formulations such as buffered or saline solutions, for example such that the naloxone content exhibits minimal degradation over periods of six months to one year or more.

Thus according to one aspect of the present invention there is provided an eyedrop composition comprising a solution of naloxone hydrochloride in a mixture of water and at least one pharmaceutically acceptable polyhydric alcohol.

The invention also embraces the use of such solutions in opioid addiction testing, e.g. as hereinbefore described.

The polyhydric alcohol preferably contains at least three hydroxyl groups per molecule and may be monomeric, for example as in glycerol, arabitol or a monosaccharide, or polymeric, for example as in polyvinyl alcohol or hydroxypropyl methylcellulose. It will be appreciated that the requirement of pharmaceutical acceptability indicates that the alcohol should not exhibit any significant harmful effects at the dosage levels employed; in this context, a typical opioid addiction test involves administration of one or two 25 μl drops to the eye. Glycerol, which is a preferred polyhydric alcohol in compositions according to the invention, is well tolerated by the eye at such levels, although it is recognised that repeated applications of glycerol may damage the endothelial cells of the cornea.

Polyhydric alcohols such as glycerol are not regarded as conventional stabilising agents, so that the stability of ophthalmically acceptable aqueous naloxone hydrochloride solutions containing such alcohols is entirely unexpected. The stability of naloxone hydrochloride solutions according to the invention may readily be confirmed by accelerated ageing techniques, for example using samples stored at 40° C., e.g. for one month; analysis for the remaining naloxone content and if desired for naloxone breakdown products such as noroxymorphone may readily be performed by HPLC. Such techniques may also be used to test the efficacies and optimum concentrations of different polyhydric alcohols.

Typically, the polyhydric alcohol may be present at concentrations in the of range 15 to 75% v/v, for example 30 to 60% v/v, advantageously at about 50% v/v. At concentrations in excess of about 40% v/v the polyhydric alcohol may have a significant viscosity enhancing effect, such that the composition may be retained on the surface of the eye for a longer period of time than are more dilute compositions, thereby enhancing absorption of naloxone through the conjunctiva and cornea, and permitting the use of more dilute naloxone hydrochloride solutions than might otherwise be practicable. Such use of relatively viscous but dilute solutions is of particular advantage in that it reduces drainage of excess naloxone into the nasal cavities, where its absorption through the nasal mucosa could trigger withdrawal symptoms in opioid dependent subjects (Sanches-Ramoz et al in *Br. J. Addiction* 82, pp. 313–315 report patients complaining of withdrawal symptoms following application of naloxone hydrochloride eyedrops with concentrations of 0.4 to 4% w/v).

Tests with aqueous glycerol systems suggest that wholly adequate retention and absorption of naloxone may be achieved at glycerol concentrations of about 50% v/v, so that no significant benefit is obtained by increasing the glycerol concentration further. Glycerol concentrations in excess of about 80% v/v are in any event preferably avoided since the viscosity of such solutions may lead to difficulties in administering the eyedrops and to discomfort of the eye, for example as a result of the solution causing resistance to movement of the eyelids.

In general the viscosity of eyedrops according to the invention may, for example, be up to about 1000 cps; preferably, however, the viscosity should be below 100 cps, most preferably between 1 and 20 cps.

The concentration of naloxone hydrochloride in compositions of the invention may, for example, be in the range 0.1 to 1.0% w/v, e.g. 0.1 to 0.4% w/v. The use of solutions comprising 0.1 or 0.2% w/v of naloxone hydrochloride and about 50% v/v of glycerol has been found to be particularly convenient; tests using such solutions and measuring anisocorial change by means of a binocular electronic pupillometer according to WO-A-94/07406 have consistently and correctly identified opioid dependent subjects with less than 20% of false negative results. Particularly importantly, control tests on non-dependent subjects using this system have been found to give no false positive results.

The compositions according to the invention may, for example, be prepared in any conventional manner, e.g. by admixture of the components under sterile conditions. Thus the polyhydric alcohol may conveniently be admixed with the aqueous component, e.g. sterile water for injection, and the naloxone hydrochloride may be dissolved in the resulting mixture; the resulting solution should be sterilised In yet another aspect, the invention provides the use of naloxone hydrochloride and a polyhydric alcohol in the preparation of a formulation as hereinbefore defined for use in opioid addiction testing.

In an alternative aspect, the present invention provides a method of diagnosing opiate dependency wherein a composition comprising naloxone hydrochloride and a polyhydric alcohol as hereinbefore defined is administered to the eye of a subject and the degree of anisocorial change is measured The publications referred to herein are hereby incorporated by reference.

The following non-limiting examples serve to illustrate the invention.

EXAMPLE 1

In a clean room solution preparation room, using sterilised equipment, a 50% v/v glycerol/water solution (1) was prepared by admixing thoroughly 60 ml glycerol and 60 ml water for injections. 0.2 g of naloxone hydrochloride was dissolved in 90 ml of the solution (1) and the resulting solution was made up to 100 ml by addition of further solution (1) with thorough mixing. The resulting 0.2%, w/v naloxone hydrochloride solution (2) was sterile filtered through two 0.22 μm filters and aseptically filled into 200 0.5 ml plastic Pasteur pipettes which were then heat sealed.

EXAMPLE 2

The procedure of Example 1 was repeated except that 0.4 g of naloxone hydrochloride was used, thereby forming a 0.4% w/v solution.

EXAMPLE 3

Samples prepared according to Examples 1 and 2 were stored at ambient temperature for periods of 50 to 72 weeks and were then analysed for naloxone content and content of the degradation product noroxymorphone by HPLC.

HPLC analysis was carried out with a Waters 501 pump, a Waters 486 variable wavelength detector and a Waters 746 data module. Separation was achieved using a Waters C18 μ-Bondapak 30 cm column.

The mobile phase was prepared by diluting 31.5 ml of 0.1 M sodium octanesulphonate, 1.00 g of sodium chloride and 1 ml of phosphoric acid to 550 ml with water filtering the resulting aqueous solution and mixing the filtrate with methanol in the proportions 67 (aqueous filtrate): 33 (methanol). The flow rate was 1.5 ml/min, and detection was carried out at 280 nm with an attenuation of 256 and injection volume of 20 μl.

Standard and sample dilutions were made using a 550:450:1 mixture of water, methanol and phosphoric acid. The standard concentration was 0.1% w/v and the samples were diluted to attain this concentration. Noroxymorphone was added to standard solutions at a concentration of 0.001% w/v. The results are summarised in the following table:

| Initial Conc. of Naloxone | Age when examined | Conc. Naloxone at test | % label strength | Conc. of Noroxymorphone |
|---|---|---|---|---|
| 0.2% | 72 weeks | 0.194% | 97% | <0.5% |
| 0.2% | 50 weeks | 0.192% | 96% | 0.5–1.0% |
| 0.2% | 50 weeks | 0.186% | 93% | — |
| 0.4% | 69 weeks | 0.389% | 97.3% | <1% |
| 0.4% | 69 weeks | 0.396% | 99% | — |

These results confirm the excellent long term storage stability of such compositions according to the invention, all samples having naloxone concentrations within 10% of label strength and no samples containing more than 1% w/v of noroxymorphone.

What is claimed is:

1. An aqueous eye drop composition which contains naloxone hydrochloride as the active ingredient and which is physiologically acceptable for ophthalmic administration and which has enhanced resistance to hydrolysis relative to saline or buffered aqueous naloxone hydrochloride solutions; said composition consisting essentially of water with naloxone hydrochloride and a polyhydric alcohol dissolved therein.

2. An eyedrop composition as claimed in claim 1 wherein the polyhydric alcohol is glycerol.

3. An eyedrop composition as claimed in claim 1 wherein said polyhydric alcohol is present at a concentration of between 30 and 60% v/v.

4. An eyedrop composition as claimed in claim 1 wherein said polyhydric alcohol is present at a concentration of about 50% v/v.

5. An eyedrop composition as claimed in claim 1 having a viscosity which is within the range of 1 to 20 CPS.

6. An eyedrop composition as claimed in claim 1 wherein the concentration of naloxone hydrochloride is in the range of 0.1 to 0.4% w/v.

* * * * *